United States Patent [19]

Suarez et al.

[11] 4,075,223

[45] Feb. 21, 1978

[54] NOVEL ANTIFERTILITY AGENTS

[75] Inventors: Tulio Suarez; C. David Jones, both of Indianapolis, Ind.

[73] Assignee: Eli Lilly and Company, Indianapolis, Ind.

[21] Appl. No.: 744,488

[22] Filed: Nov. 24, 1976

Related U.S. Application Data

[62] Division of Ser. No. 625,992, Oct. 28, 1975, Pat. No. 4,017,546.

[51] Int. Cl.$^2$ ............................................. C07D 295/10
[52] U.S. Cl. ...................... 260/326.5 C; 260/239 B; 260/293.62; 260/501.18; 260/570 R; 544/174; 544/107; 424/274

[58] Field of Search ................... 260/570 R, 326.5 J, 260/293.62, 239 B, 247.7 C, 326.5 C, 501.18

[56] References Cited

U.S. PATENT DOCUMENTS

| | | | |
|---|---|---|---|
| 2,551,316 | 5/1951 | Cusic | 260/501 |
| 4,017,546 | 4/1977 | Sharez et al. | 260/293.62 |

*Primary Examiner*—Donald G. Daus
*Assistant Examiner*—Jose Tovar
*Attorney, Agent, or Firm*—William C. Martens, Jr.; Everet F. Smith

[57] ABSTRACT

Derivatives of 2-aroyl-3-phenylindenes, 3-aroyl-4-phenyl-1,2-dihydronaphthalenes, and 1-phenyl-2-aroylnaphthalenes are useful as antifertility agents.

18 Claims, No Drawings

NOVEL ANTIFERTILITY AGENTS

This is a division, of application Ser. No. 625,992, filed Oct. 28, 1975, now U.S. Pat. No. 4,017,546.

BACKGROUND OF THE INVENTION

This invention relates to novel compounds. More particularly, this invention relates to novel compounds which possess valuable utility as antifertility agents and thus are useful in the control of animal populations. In another aspect, this invention relates to a novel method of inhibiting pregnancy and to a novel method of controlling animal populations.

The prior art has recognized various classes of compounds, each having the general formula

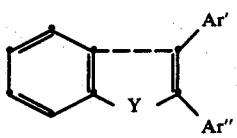

in which Ar is an aryl moiety and Y is any of various groups, such as $-CH_2-$, $-CH_2-CH_2-$, $-S-$, $-NH$, $-OCH_2-$, $-O-$, $-CH_2S-$, and $-SCH_2-$. Many compounds within these general classes are described as having antifertility activity.

Lednicer et al., *J. Med. Chem.*, 8, (1965), pp. 52–57, discloses 2,3-diphenylindenes and derivatives thereof as antifertility agents.

Lednicer et al., *J. Med. Chem.*, 9, (1966), pp. 172–175; Lednicer et al., *J. Med. Chem.*, 10 (1967), pp. 78–84; and Bencze et al., *J. Med. Chem.*, 8 (1965), pp. 213–214, each disclose various 1,2-diaryl-3,4-dihydronaphthalenes as active antifertility agents. In addition, U.S. Pat. Nos. 3,274,213; 3,313,853; 3,396,169; and 3,567,737 disclose various 1,2-diphenyl-3,4-dihydronaphthalenes as useful antifertility agents.

Other United States Patents disclose both 1,2-diphenyl-3,4-dihydronaphthalenes and 2,3-diphenylidenes as active agents. These include U.S. Pat. Nos. 3,293,263; 3,320,271; 3,483,293; 3,519,675; 3,804,851; and 3,862,232.

In addition, Crenshaw et al., *J. Med. Chem.* 14, (1971), pp. 1185–1190, disclose among others, various 2,3-diarylbenzothiophenes as exhibiting antifertility activity. Certain of these compounds are claimed in U.S. Pat. No. 3,413,305. Crenshaw et al. additionally disclose other compounds which participate in the general classes described hereinabove. 2,3-Diarylbenzofurans corresponding generally to the above benzothiophenes are disclosed and claimed in U.S. Pat. No. 3,394,125.

A need still exists to provide additional compounds useful as antifertility agents and, in particular, nonsteroidal antifertility agents. The novel compounds of this invention fill such a need. They are 2-aroyl-3-phenylindenes, 3-aroyl-4-phenyl-1,2-dihydronaphthalenes, and 1-phenyl-2-aroylnaphthalenes, and, structurally, they differ significantly from those described in the aforementioned prior art. It is an object therefore of this invention to provide novel nonsteroidal compounds having antifertility activity.

SUMMARY OF THE INVENTION

These as well as other objects are achieved by this invention which comprises a class of compounds having the formula

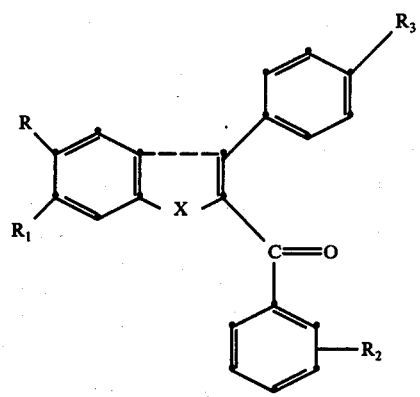

in which X is $-CH_2-$, $-CH_2-CH_2-$ or $-CH=CH-$; R and $R_1$ independently are hydrogen, hydroxyl, $C_1$- to $C_5$-alkoxy, or $C_5$- to $C_6$-cycloalkoxy; subject to the limitation that at least one of R and $R_1$ is hydrogen; $R_2$ is hydrogen, chloro, bromo, hydroxyl, $C_1$- to $C_5$-alkoxy, or $C_5$- to $C_6$-cycloalkoxy; subject to limitation that at least one of R, $R_1$, or $R_2$ is other than hydrogen; and $R_3$ is hydrogen or

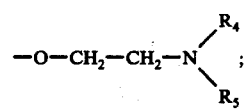

in which $R_4$ and $R_5$ independently are $C_1$–$C_4$ alkyl, or $R_4$ and $R_5$ taken together with the nitrogen to which they are bonded constitute a heterocyclic ring selected from the group consisting of pyrrolidino, piperidino, hexamethyleneimino, or morpholino; and pharmaceutically acceptable non-toxic acid addition salts of those compounds in which $R_3$ is

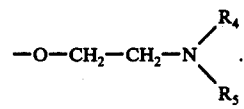

As indicated above, this invention also includes the pharmaceutically acceptable non-toxic salts of those of the above compounds in which $R_3$ is

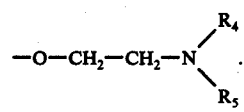

The pharmaceutically acceptable non-toxic salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, and the like. Preferably, the acid addition salts are those prepared from citric acid. Such salts are prepared by conventional methods.

The term "C₁-C₄ alkyl" as used herein contemplates both straight and branched chain groups such as methyl, ethyl, n-propyl, isopropyl, n-butyl, t-butyl, isobutyl, and sec-butyl.

The term "C₁-C₅ alkoxy" as used herein contemplates both straight and branched chain alkyl radicals and therefore defines groups such as, for example, methoxy, ethoxy, n-propoxy, isopropoxy, n-butyloxy, isobutyloxy, t-butyloxy, sec-butyloxy, n-amyloxy, isoamyloxy, t-amyloxy, sec-amyloxy, and the like.

The term "C₅-C₆ cycloalkoxy" as used herein contemplates cyclopentyloxy and cyclohexyloxy.

A preferred subclass of the compounds of this invention are the dihydronaphthalenes, that is, in the above formula, those compounds in which X is —CH₂-Ch₂—.

Of the defined dihydronaphthalenes, several preferred subclasses exist. One such subclass is comprised of 7-hydroxy-1,2-dihydronaphthalenes, that is, those compounds in which X is —CH₂-CH₂— and R₁ is hydroxyl.

Another such subclass includes the 3-(4-hydroxybenzoyl)-1,2-dihydronaphthalenes, that is, those compounds in which X is —CH₂-CH₂— and R₂ is a hydroxyl group and is located in the position para to the carbonyl function.

A further preferred subclass includes the 4-[4-(2-disubstituted aminoethoxy)phenyl]-1,2-dihydronaphthalenes, that is, those compounds in which X is —CH₂-Ch₂— and R₃ is $$-O-CH_2-CH_2-N\diagdown_{R_5}^{R_4}$$

When R₃ is so defined, it is further preferred that both R₄ and R₅ are methyl, both R₄ and R₅ are ethyl, or R₄ and R₅ taken together with the nitrogen to which they are bonded constitute a pyrrolidino ring.

The compounds of this invention are prepared by the following sequences, the dihydronaphthalene structures being precursors to the naphthalene compounds.

A. Preparation of compounds in which X is —CH₂—

These compounds are prepared from β-phenylpropionic acids of the formula

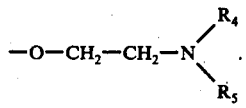

in which R₁ₐ is in the meta or para position and is hydrogen, C₁- to C₅- to C₆-cycloalkoxy, phenacyloxy, or p-halophenacyloxy. The acid is ring closed by treatment with polyphosphoric acid to produce the corresponding oxoindane

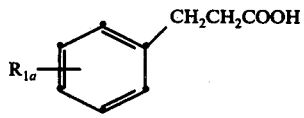

The oxoindane (II) is treated in the presence of an alkali metal amide with an ester of the formula

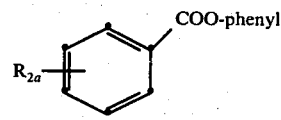

in which R₂ₐ is hydrogen, chloro, bromo, C₁- to C₅-alkoxy, C₅- to C₆-cycloalkoxy, phenacyloxy, or p-halophenacyloxy, to produce

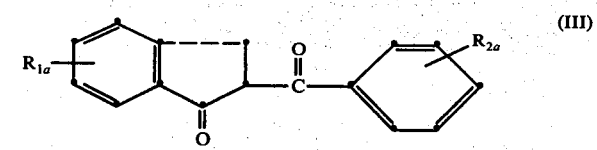

The compound III then is converted to a compound of this invention by reaction with phenylmagnesium bromide or p-methoxyphenylmagnesium bromide to produce

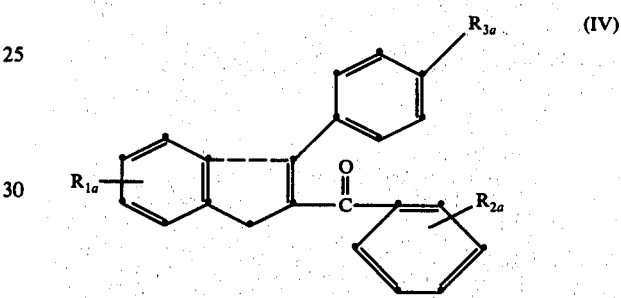

in which R₃ₐ is hydrogen or methoxyl.

When it is desired that any of R₁ₐ, R₂ₐ, and R₃ₐ be hydroxy, such is available from the corresponding alkoxy compound by treatment of the latter with pyridine hydrochloride at a temperature of from about 200° C. to about 250° C.

Selective cleavage of the methoxy groups can be accomplished by the use of reagents which preferentially attack a methoxy group located at a particular position of the molecule. Thus, if it is desired to cleave a methoxy group at R₂ₐ while retaining intact a methoxy a R₁ₐ and/or R₃ₐ, this can be accomplished using sodium thioethoxide. The compound is reacted with sodium thioethoxide in an inert solvent at a moderately elevated temperature of from about 50° C. to about 80° C. for a period sufficient to accomplish the desired reaction. The ongoing of the reaction can be monitored by periodic thin-layer chromatographic analysis (TLC) of the reaction mixture. The reaction is complete when little or no starting material remains.

When the methoxy group to be cleaved is located at R₁ₐ and/or R₃ₐ, this can be accomplished without affecting a methoxy at R₂ₐ by reacting the compound with boron tribromide. The reaction is carried out in an inert solvent, preferably methylene chloride. In the event that a methoxy group is present at both R₁ₐ and R₃ₐ, the product which results will be dependent upon both the time and temperature of the reaction. When the reaction is carried out for an extended period, for example, 20-36 hours at room temperature, both methoxy groups will be cleaved to the dihydroxy compound. This can be modified by shortening the reaction time, in which case a mixture of products will result representing cleavage either of the methoxy at $R_{1a}$ or the methoxy at $R_{3a}$. In this event the desired product can be separated from the mixture by employing standard techniques, such as chromatographic separation.

Alternatively, $R_{1a}$ and/or $R_{2a}$ can be phenacyloxy or p-halophenacyloxy, such as p-chlorophenacyloxy or p-bromophenacyloxy. Any of these phenacyl groups are suitable as protecting groups, being readily cleaved upon treatment with zinc and acetic acid at about 60° C. for approximately one hour to form the corresponding hydroxy compound. The particular sequence of synthetic steps designed to produce a compound having substituents of particular definition and location is such as one of ordinary skill in the art will well recognize.

Compounds in which $R_{3a}$ is

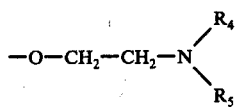

are available from the corresponding compound in which $R_3$ is hydroxy by treatment thereof in the presence of sodium hydride with a compound of the formula

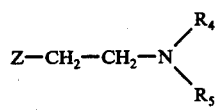

in which Z is halo, particularly bromo or chloro.

B. Preparation of compounds in which X is
—CH$_2$-CH$_2$—

These compounds are prepared by a method analogous to that desired above for preparation of the indene compounds, the principal difference being the use of a tetralone of the formula

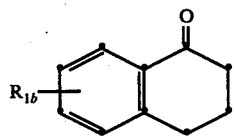

(V)

in which $R_{1b}$ is in the 6- or 7-position and is hydrogen, $C_1$- to $C_5$- alkoxy, $C_5$- to $C_6$-cycloalkoxy, phenacyloxy, or p-halophenacyloxy.

C. Preparation of compounds in which X is
—CH=CH—

These compounds are readily prepared from the aforementioned compounds in which X is —CH$_2$-CH$_2$—. Selective dehydrogenation of the dihydronaphthalene structure to produce specifically the corresponding naphthalene can be accomplished by treatment of the former with 2,3-dichloro-5,6-dicyano-1,4-benzoquinone (DDQ) at a temperature of from about 50° C. to about 100° C.

Again, by means of the aforementioned derivatizing reactions, the naphthalene which is produced can be converted to other naphthalene compounds within the scope of this invention.

The compounds of this invention are valuable pharmaceutical agents. They exhibit anti-fertility activity, and they especially are useful as orally active anti-fertility agents in birds and mammals. The compounds of this invention thus are useful in controlling the animal population and as contraceptives in living beings. The compounds of this invention also are valuable for animal pest control. For example, the compounds of this invention can be formulated in combination with baits and/or attractants and placed in feeding stations accessible to undesirable rodents and other small animals including Canidae such as coyotes, foxes, wolves, jackals, and wild dogs, and birds, such as starlings, galls, redwing blackbirds, pigeons, and the like, to greatly reduce the population thereof. By reason of the activity of the compounds of this invention, they can be used to reduce hazards to aviation by lessening the presence of birds and animals on runways and in the vicinity of air fields. The compounds of this invention also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce the inhibition of pregnancy in mammals. The usual daily dose is from about 0.02 milligrams to about 20 milligrams per kilogram body weight of the recipient. The preferred daily dose is from about 0.02 milligrams to about 0.4 milligrams per kilogram body weight of the recipient.

Examples of compounds of this invention include the following:

2-(3-hydroxybenzoyl)-3-phenylindene;
2-(2-methoxybenzoyl)-3-phenylindene;
2-(3-chlorobenzoyl)-3-phenylindene;
2-(2-bromobenzoyl)-3-phenylindene;
2-(4-isopropoxybenzoyl)-3-phenylindene;
2-(3-t-butyloxybenzoyl)-3-phenylindene;
2-(4-pentyloxybenzoyl)-3-phenylindene;
2-(3-cyclopentyloxybenzoyl)-3-phenylindene;
2-(4-cyclohexyloxybenzoyl)-3-phenylindene;
2-(3-ethoxybenzoyl)-3-phenylindene;
2-(2-hydroxybenzoyl)-3-(4-hexamethyleneiminoethoxyphenyl)indene;
2-(3-methoxybenzoyl)-3-[4-(2-dimethylaminoethoxy)-phenyl]indene;
2-(2-isopropoxybenzoyl)-3-[4-(2-diethylaminoethoxy)-phenyl]indene;
2-(4-t-butyloxybenzoyl)-3-[4-(2-pyrrolidinoethoxy)-phenyl]indene;
2-(3-pentyloxybenzoyl)-3-[4-(2-piperidinoethoxy) phenyl]indene;
2-(4-cyclopentyloxybenzoyl)-3-[4-(2-morpholinoethoxy)phenyl]indene;
2-(3-cyclohexyloxybenzoyl)-3-[4-(2-pyrrolidinoethoxy)phenyl]indene;
2-(4-chlorobenzoyl) -3-[4-(2-dimethylaminoethoxy) phenyl]indene;
2-(3-bromobenzoyl) -3-[4-(2-diethylaminoethoxy) phenyl]indene;

2-(4-methoxybenzoyl)-3-[4-(2-pyrrolidinoethoxy)phenyl]indene;
2-(3-hydroxybenzoyl)-3-[4-(2-piperidinoethoxy)phenyl]indene;
2-(4-hydroxybenzoyl)-3-[4-(2-morpholinoethoxy)phenyl]indene;
2-(4-hydroxybenzoyl)-3-phenyl-5-hydroxyindene;
2-(4-methoxybenzoyl)-3-phenyl-6-methoxyindene;
2-(4-isopropoxybenzoyl)-3-phenyl-5-ethoxyindene;
2-(3-t-butyloxybenzoyl)-3-phenyl-6-propoxyindene;
2-(4-pentyloxybenzoyl)-3-phenyl-6-cyclohexyloxyindene;
2-(3-cyclopentyloxybenzoyl)-3-phenyl-6-hydroxyindene;
2-(4-cyclohexyloxybenzoyl)-3-phenyl-5-ethoxyindene;
2-benzoyl-3-phenyl-6-methoxyindene;
2-benzoyl-3-phenyl-6-hydroxyindene;
2-benzoyl-3-(4-hexamethyleneiminoethoxyphenyl)-6-methoxyindene;
2-benzoyl-3-[4-(2-pyrrolidinoethoxy)phenyl]-5-hydroxyindene;
2-benzoyl-3-[4-(2-piperidinoethoxy)phenyl]-6-ethoxyindene;
2-benzoyl-3-[4-(2-morpholinoethoxy)phenyl]-6-ethoxyindene;
2-benzoyl-3-phenyl-5-cyclopentyloxyindene;
2-benzoyl-3-phenyl-6-pentyloxyindene;
2-benzoyl-3-phenyl-5-ethoxyindene;
2-benzoyl-3-phenyl-6-isopropoxyindene;
2-benzoyl-3-(4-hexamethyleneiminoethoxyphenyl)-5-butyloxyindene;
2-benzoyl-3-phenyl-5-hydroxyindene;
3-(3-hydroxybenzoyl)-4-phenyl-1,2-dihydronaphthalene;
3-(2-methoxybenzoyl)-4-phenyl-1,2-dihydronaphthalene;
3-(4-isopropoxybenzoyl)-4-phenyl-1,2-dihydronaphthalene;
3-(3-t-butyloxybenzoyl)-4-phenyl-1,2-dihydronaphthalene;
3-(4-pentyloxybenzoyl)-4-phenyl-1,2-dihydronaphthalene;
3-(3-cyclopentyloxybenzoyl)-4-phenyl-1,2-dihydronaphthalene;
3-(4-cyclohexyloxybenzoyl)-4-phenyl-1,2-dihydronaphthalene;
3-(4-chlorobenzoyl)-4-phenyl-1,2-dihydronaphthalene;
3-(2-bromobenzoyl)-4-phenyl-1,2-dihydronaphthalene;
3-(3-ethoxybenzoyl)-4-phenyl-1,2-dihydronaphthalene;
3-(2-hydroxybenzoyl)-4-(4-hexamethyleneiminoethoxyphenyl)-1,2-dihydronaphthalene;
3-(3-methoxybenzoyl)-4-[4-(2-dimethylaminoethoxy)phenyl]-1,2-dihydronaphthalene;
3-(2-isopropoxybenzoyl)-4-[4-(2-diethylaminoethoxy)phenyl]-1,2-dihydronaphthalene;
3-(4-t-butyloxybenzoyl)-4-[4-(2-pyrrolidinoethoxy)phenyl]-1,2-dihydronaphthalene;
3-(3-pentyloxybenzoyl)-4-[4-(2-piperidinoethoxy)phenyl]-1,2-dihydronaphthalene;
3-(4-cyclopentyloxybenzoyl)-[4-(2-morpholinoethoxy)phenyl]-1,2-dihydronaphthalene;
3-(3-cyclohexyloxybenzoyl)-4-[4-(2-pyrrolidinoethoxy)phenyl]-1,2-dihydronaphthalene;
3-(4-chlorobenzoyl)-4-[4-(2-dimethylaminoethoxy)phenyl]-1,2-dihydronaphthalene;
3-(3-bromobenzoyl)-4-[4-(2-diethylaminoethoxy)phenyl]-1,2-dihydronaphthalene;
3-(4-methoxybenzoyl)-4-[4-(2-pyrrolidinoethoxy)phenyl]-1,2-dihydronaphthalene;
3-(3-hydroxybenzoyl)-4-[4-(2-piperidinoethoxy)phenyl]-1,2-dihydronaphthalene;
3-(4-hydroxybenzoyl)-4-[4-(2-morpholinoethoxy)phenyl]-1,2-dihydronaphthalene;
3-(4-hydroxybenzoyl)-4-phenyl-6-hydroxy-1,2-dihydronphthalene;
3-(4-methoxybenzoyl)-4-phenyl-7-methoxy-1,2-dihydronaphthalene;
3-(4-isopropoxybenzoyl)-4-phenyl-6-ethoxy-1,2-dihydronaphthalene;
3-(3-t-butyloxybenzoyl)-4-phenyl-7-propoxy-1,2-dihydronaphthalene;
3-(4-pentyloxybenzoyl)-4-phenyl-7-cyclohexyloxy-1,2-dihydronaphthalene;
3-(3-cyclopentyloxybenzoyl)-4-phenyl-7-hydroxy-1,2-dihydronaphthalene;
3-(4-cyclohexyloxybenzoyl)-4-phenyl-6-ethoxy-1,2-dihydronaphthalene;
3-benzoyl-4-phenyl-7-methoxy-1,2-dihydronaphthalene;
3-benzoyl-4-phenyl-7-hydroxy-1,2-dihydronaphthalene;
3-benzoyl-4-(4-hexamethyleneiminoethoxyphenyl)-7-methoxy-1,2-dihydronaphthalene;
3-benzoyl-4-[4-(2-pyrrolidinoethoxy)phenyl]-6-hydroxy-1,2-dihydronaphthalene;
3-benzoyl-4-[4-(2-piperidinoethoxy)phenyl]-7-ethoxy-1,2-dihydronaphthalene;
3-benzoyl-4-[4-(2-morpholinoethoxy)phenyl]-7-methoxy-1,2-dihydronaphthalene;
3-benzoyl-4-phenyl-6-cyclopentyloxy-1,2-dihydronaphthalene;
3-benzoyl-4-phenyl-7-pentyloxy-1,2-dihydronaphthalene;
3-benzoyl-4-phenyl-6-ethoxy-1,2-dihydronaphthalene;
3-benzoyl-4-phenyl-7-isopropoxy-1,2-dihydronaphthalene;
3-benzoyl-4-(4-hexamethyleneiminoethoxyphenyl)6-butyloxy-1,2-dihydronaphthalene;
3-benzoyl-4-phenyl-6-hydroxy-1,2-dihydronaphthalene;
1-phenyl-2-(3-hydroxybenzoyl)naphthalene;
1-phenyl-2-(4-chlorobenzoyl)naphthalene;
1-phenyl-2-(2-bromobenzoyl)naphthalene;
1-phenyl-2-(2-methoxybenzoyl)naphthalene;
1-phenyl-2-(4-isopropoxybenzoyl)naphthalene;
1-phenyl-2-(3-t-butyloxybenzoyl)naphthalene;
1-phenyl-2-(4-pentyloxybenzoyl)naphthalene;
1-phenyl-2-(3-cyclopentyloxybenzoyl)naphthalene;
1-phenyl-2-(4-cyclohexyloxybenzoyl)naphthalene;
1-phenyl-2-ethoxybenzoylnaphthalene;
1-(4-hexamethyleneiminoethoxyphenyl)-2-(2-hydroxybenzoyl)naphthalene;
1-[4-(2-dimethylaminoethoxy)phenyl]-2-(3-methoxybenzoyl)naphthalene;
1-[4-(2-diethylaminoethoxy)phenyl]-2-(2-isopropoxybenzoyl)naphthalene;
1-[4-(2-pyrrolidinoethoxy)phenyl]-2-(4-t-butyloxybenzoyl)naphthalene;
1-[4-(2-piperidinoethoxy)phenyl]-2-(3-penthloxybenzoyl)naphthalene;
1-[4-(2-morpholinoethoxy)phenyl]-2-(4-cyclopentyloxybenzoyl)naphthalene;
1-[4-(2-pyrrolidinoethoxy)phenyl]-2-(3-cyclohexyloxybenzoyl)naphthalene;

1-[4-(2-dimethylaminoethoxy)phenyl]-2-(4-chlorobenzoyl)naphthalene;
1-[4-(2-diethylaminoethoxy)phenyl]-2-(3-bromobenzoyl)naphthalene;
1-[4-(2-pyrrolidinoethoxy)phenyl]-2-(4-methoxybenzoyl)naphthalene;
1-[4-(2-piperidinoethoxy)phenyl]-2-(2-hydroxybenzoyl)naphthalene;
1-[4-(2-morpholinoethoxy)phenyl]-2-(4-hydroxybenzoyl)naphthalene;
1-phenyl-2-(4-hydroxybenzoyl)-6-hydroxynaphthalene;
1-phenyl-2-(4-methoxybenzoyl)-7-methoxynaphthalene;
1-phenyl-2-(4-isopropoxybenzoyl)-6-ethoxynaphthalene;
1-phenyl-2-(3-t-butyloxybenzoyl)-7-propoxynaphthalene;
1-phenyl-2-(4-pentyloxybenzoyl)-7-cyclohexyloxynaphthalene;
1-phenyl-2-(3-cyclopentyloxybenzoyl)-7-hydroxynaphthalene;
1-phenyl-2-(4-cyclohexyloxybenzoyl)-6-ethoxynaphthalene;
1-phenyl-2-benzoyl-7-methoxynaphthalene;
1-phenyl-2-benzoyl-7-hydroxynaphthalene;
1-(4-hexamethyleneiminoethoxyphenyl)-2-benzoyl-7-methoxynaphthalene;
1-[4-(2-pyrrolidinoethoxy)phenyl]-2-benzoyl-6-hydroxynaphthalene;
1-[4-(2-piperidinoethoxy)phenyl]-2-benzoyl-7-ethoxynaphthalene;
1-[4-(2-morpholinoethoxy)phenyl]-2-benzoyl-7-methoxynaphthalene;
1-phenyl-2-benzoyl-6-cyclopentyloxynaphthalene;
1-phenyl-2-benzoyl-7-pentyloxynaphthalene;
1-phenyl-2-benzoyl-6-ethoxynaphthalene;
1-phenyl-2-benzoyl-7-isopropoxynaphthalene;
1-(4-hexamethyleneiminoethoxyphenyl)-2-benzoyl-6-butyloxynaphthalene;
1-phenyl-2-benzoyl-6-hydroxynaphthalene; and the like.

The following examples are illustrative of the preparation and activities of the compounds of this invention. They are not intended to be limiting upon the broad scope thereof.

EXAMPLE 1

Preparation of 2-(4-Methoxybenzoyl)-3-phenyl-6-methoxyindene.

A mixture of 5 gms. of β-(3-methoxyphenyl)-propionic acid in polyphosphoric acid was prepared. The mixture was heated for 2 hours at 120° C. The mixture then was cooled, and ice was added. The resulting solid was removed by filtration and dissolved in benzene. The benzene solution was filtered and concentrated to one-fourth volume. Petroleum ether was added and the mixture was cooled to 5° C. The product, 1-oxo-5-methoxyindane was collected by filtration, m.p. 105°-107° C.

Anaylsis, Calcd. for $C_{10}H_{10}O_2$: C, 74.06; H, 6.22; O, 19.73. Found: C, 74.32, H, 6.42; O, 20.03.

A solution of 22.2 gms. (0.137 mole) of the oxoindane in tetrahydrofuran (THF) was added dropwise to a cold suspension of 11 gms. (0.274 mole) of sodium amide in THF. The resulting mixture was stirred for 10 minutes, and a solution of 31.3 gms. (0.137 mole) of phenyl p-methoxybenzoate in THF was added. Cooling was discontinued, and a slight exothermic reaction occurred. The mixture was stirred at room temperature for 2 hours. A thick precipitate developed, and the reaction mixture was poured into ice-water. The aqueous mixture then was extracted with ethyl acetate to obtain 20.7 gms. of 1-oxo-2-(4-methoxybenzoyl)-5-methoxyindane, m.p. 160°-162° C.

A slurry of 20.5 gms. (0.0694 mole) of the diketone prepared above in benzene was added as a slow stream to solution of a five-fold excess of phenyl magnesium bromide in ether. The resulting mixture then was refluxed for 4 hours. The mixture was cooled and poured into a mixture of ice and sulfuric acid. The mixture then was extracted with ethyl acetate, washed with water and then with aqueous sodium bicarbonate, and dried over magnesium sulfate. The mixture then was concentrated to 28 gms. of a dark red oil. A mixture of 20 percent ether in methanol (25 ml.) was added. Part of the oil crystallized on standing at room temperature and was isolated by filtration to obtain 7.5 gms. of red-brick crystals. This material was slurried in a hot mixture of benzene and acetone. The insoluble solid was separated by filtration. The filtrate was concentrated to dryness, and the residue was recrystallized from ether to obtain 5.4 gms. of the product, m.p. 113°-114° C.

The filtrate from the aforementioned separation of the red-brick crystals was concentrated and chromatographed on silica with benzene as eluant. From this chromatographic separation were obtained an additional 3 gms. of the title compound, m.p. 113°-114° C.

These two portions of product were combined, recrystallized from acetone, and air dried to obtain the title compound, m.p. 115°-116° C.

Analysis, Calcd. for $C_{24}H_{20}O_3$: C, 80.88; H, 5.66; O, 13.47. Found: C, 80.95; H, 5.84; O, 14.42.

EXAMPLE 2

PREPARATION OF 2-(4-METHOXYBENZOYL)-3-PHENYLINDENE.

A slurry of 13.25 gms. (0.05 mole) of 1-oxy-2-(4-methoxybenzoyl)indane (prepared by a sequence analoqous to that described in Example 1) in a mixture of 300 ml. of ether and 200 ml. of benzene was prepared. To the slurry were added 35.657 gms. (0.197 mole) of phenylmagnesium bromide. The resulting mixture was refluxed overnight. The mixture then was poured into a mixture of ice and sulfuric acid, and the resulting organic layer was separated, washed with aqueous sodium bicarbonate solution, and dried over sodium sulfate. The organic solution then was concentrated to a red residue. The residue was dissolved in a small amount of ether and cooled. White-pink crystals (2.0 gms.) formed and were collected by filtration, m.p. 200°-202° C.

The filtrate was concentrated to dryness, and the residue crystallized on standing. Methanol was added to the residue, and the mixture was filtered to abtain 9.3 gms. of the title compound, m.p. 114°-115° C.

Analysis, Calcd. for $C_{23}H_{18}O_2$: C, 84.64; H, 5.56; O, 9.80. Found: C, 84.69; H, 5.82; O, 9.79.

EXAMPLE 3

PREPARATION OF 2-(4-HYDROXYBENZOYL)-3-PHENYL-6-HYDROXYINDENE.

To a solution of 4 gms. of the product from Example 1 in dichloromethane were added two equivalents of boron tribromide. The resulting mixture was stirred for 24 hours. Analysis of the reaction mixture by TLC indicated the presence of starting material, product, and some of the monohydroxy compound. Another equivalent of boron tribromide was added, and the mixture was stirred for a total of 72 hrs. TLC indicated no starting material and only traces of the monohydroxy derivative. The product was chromatographed on silica using a mixture of 10 percent ethyl acetate and 90 percent benzene to obtain 3 gms. of the title compound, m.p. 191°–192° C.

Analysis, Calcd. for $C_{22}H_{16}O_3$: C, 80.47; H, 4.91; O, 14.62. Found: C, 80.28; H, 4.98; O, 14.71.

EXAMPLE 4

PREPARATION OF 3-(4-METHOXYBENZOYL)-4-PHENYL-7-METHOXY-1,2-DIHYDRONAPHTHALENE.

To a suspension of 10.5 gms. of sodium amide in THF were added 23.2 gms. of 6-methoxy-α-tetralone in THF. The resulting mixture was stirred for 10 minutes, and a solution of 30 gms. of phenyl p-methoxybenzoate in THF was added. The resulting mixture was stirred at room temperature overnight. The THF then was concentrated in vacuo. Water was added to the residue. The solid that did not dissolve in the water was removed by filtration and slurried in hot methanol. The methanol was cooled to room temperature and filtered to give 24.3 gms. of 2-(4-methoxybenzoyl)-6-methoxy-α-tetralone, m.p. 112°–113° C.

Analysis, Calcd. For $C_{19}H_{18}O_4$: C, 73.53; H, 5.85; O, 20.62 Found: C, 72.23; H, 6.55; O, 2.67

Mass spectrum: Theory, 310; Found, 310.

To 500 ml. of a 1:1 mixture of ether and benzene were added 21.7 gms. (0.07 mole) of the above-prepared tetralone. The resulting slurry was added to 146 ml. of a 2.05 molar solution of phenylmagnesium bromide in ether (represents 0.3 moles of phenylmagnesium bromide). The resulting mixture turned green and was refluxed for 4 hours. The mixture then was poured into a mixture of ice and sulfuric acid. The resulting mixture then was extracted with ethyl acetate. The ethyl acetate extract was washed successively with water, aqueous sodium bicarbonate, and water, and then was dried over magnesium sulfate. The ethyl acetate solution was concentrated to dryness, and the residue, a red-yellow oil, was crystallized from ether to obtain 13.8 gms. of the title compound as white crystals, m.p. 107°–108° C. Analysis, Calcd. for $C_{25}H_{22}O_3$: C, 81.06; H, 5.99; O, 12.96. Found: C, 81.14; H, 5.79; O, 12.93.

Mass spectrum: Theory, 370; Found, 370; 339

EXAMPLE 5

Preparation of 3-(4-Hydroxybenzoyl)-4-phenyl-7-hydroxy-1,2-dihydronaphthalene.

To 300 ml. of DMF were added under nitrogen and with ice bath cooling, 9.3 gms. of ethyl mercaptan. To the mixture then were added 7.2 gms. of a 50 percent sodium hydride-oil mixture. The mixture represents 0.15 mole of sodium hydride. To the resulting mixture then were added 11.1 gms. (0.03 mole) of the product from Example 1. The mixture was heated at 60° C. for 1 hour. Analysis of the reaction mixture by TLC indicated the presence of starting material plus another component, probably the mono-hydroxy compound. The temperature of the reaction mixture was raised to 110° C., and this temperature was maintained for one hour. TLC showed no starting material; however, the presence of two components was noted. The reaction mixture therefore was heated for an additional one hour at 125° C. after which a single spot was noted by TLC analysis. The reaction mixture then was acidified by addition of cold 1N hydrochloric acid. The mixture was extracted with ethyl acetate. The ethyl acetate was washed with water and evaporated. The resulting residue was recrystallized from a mixture of methanol and acetone to give 8 g. of the title compound, m.p. 205°–207° C.

Analysis, Calcd. for $C_{23}H_{18}O_3$: C, 80,68; H, 5.30; O, 14.02. Found: C, 80.38; H, 5.43; O, 14.28.

EXAMPLE 6

Preparation of 1-Phenyl-2-(4-methoxybenzoyl)-6-methoxynaphthalene.

To 11.1 g. (0.03 mole) of the product from Example 4 dissolved in benzene were added 9.0 g. of 2,3-dichloro-5,6-dicyano-1,4-benzoquinone (DDQ). The mixture was refluxed for two hours and then was filtered while hot through silica, and the silica was washed three times with ethyl acetate. The ethyl acetate washings were combined with the benzene reaction mixture, and the total was concentrated to dryness. The residue was dissolved in hot methanol, and the solution was allowed to cool to obtain 4.5 g. of product. The product was recrystallized again from methanol to obtain the title compound, m.p. 122°–124° C.

Analysis, Calcd. for $C_{25}H_{20}O_3$: C, 81.50; H, 5.47; O, 13.03. Found: C, 81.52; H, 5.68; O, 12.93.

Mass spectrum; Theory, 368; Found, 368.

The compounds of this invention are tested for antifertility activity in accordance with the following procedure:

Fifty young adult virgin female rats weighing 200–230 g. each are separated into ten groups of five each. One of the groups serves as the control group and the other nine groups as experimental groups, each such experimental group receiving test compound at a particular dose level. The test compound for each group of five rats is prepared in corn oil such that the daily administration is in 0.1 ml. of vehicle. The designated quantity of the test compound in the vehicle is administered to each rat within the defined group subcutaneously (sc) daily. The control group receives only the vehicle. Administration of the vehicle or the combination of test compound and vehicle is continued on a daily basis for 15 days. On the 5th day of treatment, two adult male rats weighing at least 250 g. each are added to each group, and cohabitation is continued until the 15th day at which time the male rats are withdrawn from the group. Each group of female rats then is maintained for an additional 7 days after which the rats are sacrificed and examined for the presence of viable or resorbing fetuses.

The number of animals that exhibit evidence of pregnancy over the number of animals in the group is the pregnancy ratio. A compound is considered active when the ratio is 0/5 or 1/5. A ratio of 2/5 consitutes marginal activity, and anything higher is inactive.

The Table following illustrates the antifertility activity of compounds of this invention.

Table
Antifertility Activity

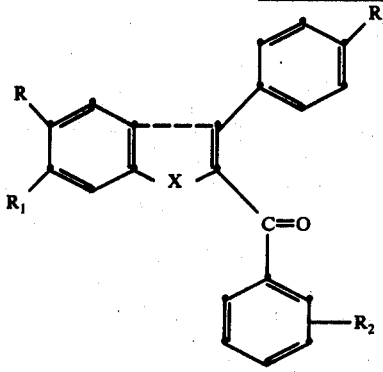

| R | $R_1$ | $R_2$ | $R_3$ | X | dose mg./day | Pregnancy Ratio P/5 P = |
|---|---|---|---|---|---|---|
| H | H | 4-OCH$_3$ | H | —CH$_2$— | 1.0 | 0$^a$ |
|   |   |   |   |   | 0.1 | 0 |
|   |   |   |   |   | 0.05 | 4 |
| H | —OCH$_3$ | 4-OCH$_3$ | H | —CH$_2$— | 5.0 | 0 |
|   |   |   |   |   | 1.0 | 0 |
|   |   |   |   |   | 0.5 | 0$^a$ |
|   |   |   |   |   | 0.1 | 0$^b$ |
|   |   |   |   |   | 0.5 | 0 |
|   |   |   |   |   | 0.01 | 4 |
|   |   |   |   |   | 0.005 | 4 |
| H | —OCH$_3$ | 4-OCH$_3$ | H | —CH$_2$—CH$_2$— | 1.0 | 0 |
|   |   |   |   |   | 0.5 | 0 |
|   |   |   |   |   | 0.1 | 1 |
|   |   |   |   |   | 0.05 | 3 |
| H | —OH | 4-OH | H | —CH$_2$— | 0.5 | 0 |
|   |   |   |   |   | 0.05 | 0 |
|   |   |   |   |   | 0.01 | 0 |
|   |   |   |   |   | 0.005 | 0 |
|   |   |   |   |   | 0.001 | 4 |
|   |   |   |   |   | 0.0005 | 4 |
| H | —OH | 4-OH | H | —CH$_2$—CH$_2$— | 0.5 | 0$^a$ |
|   |   |   |   |   | 0.1 | 0 |
|   |   |   |   |   | 0.05 | 0 |
|   |   |   |   |   | 0.01 | 4 |
|   |   |   |   |   | 0.005 | 5 |
| H | —OCH$_3$ | 4-OCH$_3$ | H | —CH=CH— | 5.0 | 2 |
|   |   |   |   |   | 1.0 | 3 |

$^a$Pregnancy ratio is 0/4.
$^b$Pregnancy ratio is 0/3.

We claim:
1. A compound of the formula

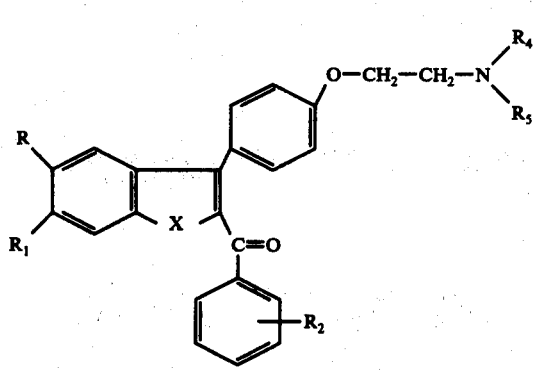

in which X is —CH$_2$—, —CH$_2$-CH$_2$— or —CH=CH—; R and R$_1$ independently are hydrogen, hydroxyl, C$_1$- to C$_5$-alkoxy, or C$_5$- to C$_6$-cycloalkoxy; subject to the limitation that at least one of R and R$_1$ is hydrogen; R$_2$ is hydrogen, chloro, bromo, hydroxyl, C$_1$- to C$_5$-alkoxy, or C$_5$- to C$_6$-cycloalkoxy; subject to the limitation that at least one of R, R$_1$, or R$_2$ is other than hydrogen; and R$_4$ and R$_5$ independently are C$_1$-C$_4$ alkyl, or R$_4$ and R$_5$ taken together with the nitrogen to which they are bonded constitute a heterocyclic ring selected from the group consisting of pyrrolidino, piperidino, hexamethyleneimino, or morpholino; and pharmaceutically acceptable non-toxic acid addition salts thereof.

2. Compound of claim 1, in which X is —CH$_2$-CH$_2$—.
3. Compound of claim 2, in which R$_1$ is hydroxyl.
4. Compound of claim 2, in which R$_2$ is hydroxyl.
5. Compound of claim 4, in which the R$_2$ substituent is in the para position.
6. Compound of claim 5, in which R$_1$ is hydroxyl.
7. Compound of claim 2, in which R$_4$ and R$_5$ are methyl.
8. Compound of claim 2, in which R$_4$ and R$_5$ are ethyl.
9. Compound of claim 2, in which R$_4$ and R$_5$ taken together with the nitrogen to which they are bonded constitute a pyrrolidino function.
10. Compound of claim 2, in the form of its pharmaceutically acceptable non-toxic salt.
11. Compound of claim 10, in the form of its citrate salt.
12. Compound of claim 1, in which X is —CH$_2$—.
13. Compound of claim 12, in which R$_1$ is hydroxyl.
14. Compound of claim 12, in which R$_2$ is hydroxyl.
15. Compound of claim 14, in which the R$_2$ substituent is in the para position.
16. Compound of claim 15, in which R$_1$ is hydroxyl.
17. Compound of claim 15, in which R$_1$ is methoxy.
18. Compound of claim 1, in which X is —CH=CH—.

* * * * *